(12) United States Patent
Borland, Jr.

(10) Patent No.: US 7,754,237 B1
(45) Date of Patent: Jul. 13, 2010

(54) TRANSDERMAL THIAMINE INSECT REPELLANT

(76) Inventor: Robert E. Borland, Jr., 12158 Highway 231 North, Pinckard, AL (US) 36371

( * ) Notice: Subject to any disclaimer, the term of this patent is extended or adjusted under 35 U.S.C. 154(b) by 259 days.

(21) Appl. No.: 11/191,606

(22) Filed: Jul. 28, 2005

Related U.S. Application Data

(60) Provisional application No. 60/592,296, filed on Jul. 29, 2004.

(51) Int. Cl.
*A61F 13/00* (2006.01)
*A01N 25/34* (2006.01)
*A61K 31/51* (2006.01)

(52) U.S. Cl. .................. 424/449; 424/403; 514/276

(58) Field of Classification Search .............. 424/405, 424/449, 403; 514/276
See application file for complete search history.

(56) References Cited

U.S. PATENT DOCUMENTS

| | | | |
|---|---|---|---|
| 4,876,090 A | 10/1989 | Weisler | |
| 5,021,424 A | 6/1991 | Lawton-Wall | |
| 5,899,856 A * | 5/1999 | Schoendorfer et al. | 600/362 |
| 5,965,137 A | 10/1999 | Petrus | |
| 6,010,715 A * | 1/2000 | Wick et al. | 424/448 |
| 6,475,514 B1 * | 11/2002 | Blitzer et al. | 424/449 |
| 6,719,997 B2 | 4/2004 | Hsu et al. | |
| 6,858,200 B2 | 2/2005 | Fowler | |
| 2005/0008656 A1 | 1/2005 | Meredith | |

\* cited by examiner

*Primary Examiner*—Shanon A Foley
(74) *Attorney, Agent, or Firm*—Buskop Law Group, PC; Wendy Buskop

(57) ABSTRACT

A method for repelling insects from the skin of a subject by applying thiamine to the skin in a transdermal patch in an effective amount for systemic absorption through the skin. The area of transdermal patch which contacts the skin is about 35 cm$^2$, and the amount of thiamine in the transdermal patch is about 50 mg. After application, the transdermal patch provides insect repelling activity up to 48 hours.

15 Claims, No Drawings

TRANSDERMAL THIAMINE INSECT REPELLANT

CROSS REFERENCE TO RELATED APPLICATIONS

This non-provisional patent application claims priority to U.S. Provisional Patent Application No. 60/592,296 filed Jul. 29, 2004, incorporated herein by reference.

BACKGROUND OF THE INVENTION

1. Field of the Invention

This invention relates to methods for repelling insects and, more particularly, to the transdermal systemic delivery of thiamine to repel insects.

2. Technical Background

Insect repellants are useful for preventing insects from biting the skin, especially mosquitoes. Most of the known insect repellants that are topically applied to deter mosquitoes from biting consist of chemical compositions consisting of: N, N-diethyl toluamide (DEET), N, N-diethyl benzamide, dimethyl phytate, ethyl bexanediol, indalone, di-n-propyl-isocinchoronate, bicycloheptene dicarboxide, tetrahydro furaldehyde, among others. DEET, the most popular, is toxic and known to cause skin irritation, irritability, and seizures. Indalone and ethyl bexanediol are known to cause liver and kidney damage. Topical application of these agents requires the use of formulations that produce oily or greasy unpleasant residues on the skin. These formulations also produce unpleasant odors.

Oral administration of garlic is known to repel insects, but garlic can produce unpleasant odors after ingestion, and is only marginally effective as an insect repellant.

Oral administration of thiamine (vitamin $B_1$) has also been used to repel insects. Thiamine is excreted in the sweat and releases an odor on the surface of the skin which is offensive to insects such as mosquitoes but is imperceptible to humans. The oral administration of thiamine as a single agent has not been adequately effective in this regard, probably because of variable gastrointestinal absorption and first pass extraction by the liver. Thiamine delivered orally needs to be administered with other agents such as garlic or vitamin C plus biotin, or one or more herbs to have effective insect repellant activity.

What is needed is an effective systemic delivery of thiamine that produces a consistent and sustained insect repellant effect without the need for additional agents.

SUMMARY OF THE INVENTION

The present invention provides a method of repelling insects using a transdermal patch contain about 50 mg of thiamine. The patch has a thin film backing as the occlusive support membrane. A pressure-sensitive adhesive is coated on to one side of this film. This adhesive contains thiamine that has been dispersed into an adhesive resin. The adhesive element is protected by a liner which is removed from the adhesive prior to application to the skin of the patch to the skin. The patch is applied, preferably, two or more hours before protection is needed against insects. The backing is removed from the patch and the patch is placed on clean, hairless, dry skin. The patch is worn 24 to 48 hours to insure protection up to 6 hours after it is removed. The patch containing thiamine will, thus, deliver up to 48 hours of protection from biting insects, particularly mosquitoes, flies, and/or midges.

An advantage of the present invention is the ability to repel insects by the systemic delivery of thiamine into the blood stream through the skin.

Another advantage is the ability to repel insects without the use of oily creams or ointments.

Another advantage is 48 hour protection against insects.

Another advantage is an insect repellant that is a natural vitamin with excellent safety.

Another advantage is an insect repellant that is simple to manufacture and use.

DETAILED DESCRIPTION OF THE PREFERRED EMBODIMENTS

The present invention for administering thiamine systemically (into the blood stream) uses a topical or transdermal "patch," wherein the thiamine is contained within a structure that is to be affixed to the skin. In such a structure, the thiamine is contained in a layer, or "reservoir," underlying an upper backing layer. The reservoir has a polymeric matrix of a pharmaceutically acceptable adhesive material that serves to affix the system to the skin during thiamine delivery. The adhesive material is usually a pressure-sensitive adhesive (PSA) that is suitable for long-term skin contact, and which should be physically and chemically compatible with thiamine, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes and polyacrylates.

During storage and prior to use, the structure includes a release liner. Immediately prior to use, this layer is removed from the device so that the system may be affixed to the skin. The release liner should be made from a thiamine vehicle impermeable material, and is a disposable element which serves only to protect the device prior to application. Typically, the release liner is formed from a material impermeable to thiamine and which is easily stripped from the transdermal patch prior to use.

The thiamine reservoir and skin contact adhesive may be present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or may be a hydrogel reservoir, or may take some other form. Hydrogels may be comprised of crosslinked hydrophilic polymers such as a polyurethane, a polyvinyl alcohol, a polyacrylic acid, a polyoxyethylene, a polyvinylpyrrolidone, a polyhydroxyethyl methacrylate (polyHEMA), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these transdermal delivery systems. Fabric layers may be used to facilitate fabrication of the device, while a rate-controlling membrane may be used to control the rate at which thiamine permeates out of the device.

A rate-controlling membrane, if present, is included in the system on the skin side of one or more of the ingredient reservoirs. The materials used to form such a membrane are selected to limit the flux of thiamine contained in the formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 cm$^2$ to 200 cm$^2$, preferably 5 cm$^2$ to 100 cm$^2$, more preferably about 36 cm$^2$. That area will vary, of course, with the amount of thiamine to be delivered and the flux of the thiamine through the body surface. Larger patches will be necessary to accommodate larger quantities of thiamine, while smaller patches can be used for small quantities of thiamine.

The backing layer functions as the primary structural element of the transdermal system and provides the device with flexibility and, preferably, occlusivity. The material used for the backing layer should be inert and incapable of absorbing thiamine or components of the formulation contained within the device. The backing is preferably comprised of a flexible elastomeric material that serves as a protective covering to prevent loss of thiamine and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

The transdermal delivery systems of the present invention may be fabricated using conventional coating and laminating techniques known in the art. For example adhesive matrix systems can be prepared by casting a fluid admixture adhesive, thiamine and vehicle onto the backing layer followed by lamination of the release liner. Similarly the adhesive mixture may be cast onto the release liner, followed by lamination of the release liner. Alternatively, the ingredient reservoir may be prepared in the absence of thiamine or excipient, and then loaded by "soaking" in a thiamine/vehicle mixture. In general, transdermal systems of the invention are fabricated by solvent evaporation, film casting, melt extrusion, thin film lamination, die cutting, or the like. The thiamine may be incorporated into the device during patch manufacture or subsequent to preparation of the device.

In some cases, the thiamine may be delivered "neat," i.e., in the absence of additional liquid. In other cases, the thiamine can be dissolved, dispersed or suspended in a suitable pharmaceutically acceptable vehicle, typically a solvent or gel. Other components which may be present include preservatives, stabilizers, surfactants, and the like.

The practice of the present invention will employ conventional techniques of formulation, particularly topical formulation, which are within the skill of the art. The invention, accordingly, provides a highly effective means for systemically administering thiamine through the skin of a human or animal for use as an insect repellant.

In a preferred embodiment, a 36 cm$^2$ transdermal patch contains about 10 to 300 mg of thiamine, preferably about 50 mg of thiamine. The patch consists of a thin polyolefin film (polyethylene) as the occlusive support membrane. A pressure-sensitive adhesive reservoir is coated on to one side of this film. This adhesive consists of thiamine that has been dispersed into an acrylic multi-polymer adhesive resin. Also included in the adhesive mass is a small amount of a monomeric ester plasticizer that will provide improved flow and adhesion on the skin. The adhesive mass is protected by a silicone-coated supercalendered kraft paper liner which is removed from the adhesive prior to application to the skin.

The patch is applied to the skin of a subject, preferably two or more hours before protection is needed against biting insects. The liner is removed from the patch and the patch is placed on clean, hairless, dry skin. It may be desirable to clean the skin with solvents that remove water-soluble and/or lipid-soluble dirt and debris. The thiamine is transported from the reservoir, through the skin, and into the blood stream. The thiamine is then excreted in the sweat of the subject, releasing an odor on the surface of the skin which repels insects. The patch should be worn 24-48 hours to insure protection up to 6 hours after it is removed. The patch containing thiamine will, thus, deliver up to 48 hours of protection to a subject from biting insects, particularly mosquitoes, flies, and/or midges (no-see-em's).

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, any salt of thiamine may be used, such as monochloride, diphosphate, triphosphate, or disulfide, preferably monochloride. Other active agents can be added to the thiamine, such as, for example, oil of garlic. Other types and configurations of transdermal drug delivery systems may be used to deliver thiamine systemically, as disclosed in U.S. Pat. No. 6,719,997, which is incorporated herein by reference. The transdermal patch may be provided as a kit containing a cleaning element to clean the skin where the patch is to be applied, a transdermal patch having a backing and an adhesive reservoir containing thiamine, and a liner covering the adhesive reservoir where the liner is removed prior to applying the patch to the skin. The cleaning element, such as a cloth or sponge, may contain solvents to remove water-soluble and/or lipid-soluble debris and dirt from the skin.

It will be understood that various changes in the details, materials, and arrangements of the parts which have been described and illustrated above in order to explain the nature of this invention may be made by those skilled in the art without departing from the principle and scope of the invention as recited in the following claims.

What is claimed is:

1. A transdermal delivery patch for protecting a subject from mosquitoes, flies, midges, or combinations thereof, consisting of:
    i. a backing;
    ii. from about 10 mg to about 300 mg thiamine blended throughout a pressure-sensitive adhesive matrix, wherein a backing side of the pressure-sensitive adhesive matrix is disposed on at least a portion of the backing; and
    iii. a liner removable disposed on a skin side of the pressure-sensitive adhesive matrix opposite the backing.

2. The transdermal delivery patch of claim 1, wherein the pressure-sensitive adhesive matrix comprises an acrylic multi-polymer adhesive resin and the thiamine.

3. The transdermal delivery patch of claim 2, wherein pressure-sensitive adhesive matrix further comprises a monomeric ester plasticizer.

4. The transdermal delivery patch of claim 1, wherein the backing is occlusive or permeable.

5. The transdermal delivery patch of claim 1, wherein the backing is a synthetic polymer.

6. The transdermal delivery patch of claim 1, wherein the transdermal patch has a skin contact area of about 5 cm$^2$ to about 100 cm$^2$.

7. The transdermal delivery patch of claim 1, wherein the adhesive comprises at least one of polyethylenes, polysiloxanes, polyisobutylenes, polyacrylates, polyacrylamides, polyurethanes, plasticized ethylene-vinyl acetate copolymers, and tack rubbers.

8. A kit for repelling insects comprising:
   a. a transdermal delivery patch for protecting a subject from mosquitoes, flies, midges, or combinations thereof, consisting of:
      i. a backing;
      ii. from about 10 mg to about 300 mg of thiamine blended throughout a pressure-sensitive adhesive matrix, wherein a backing side of the pressure-sensitive adhesive matrix is disposed on at least a portion of the backing; and
      iii. a liner removable disposed on a skin side of the pressure-sensitive adhesive matrix opposite the backing; and
   b. a cleaning element.

9. A method for repelling insects from a subject, the method comprising:
   a. applying a transdermal delivery patch for protecting a subject from mosquitoes, flies, midges, or combinations thereof for at least twenty-four hours allowing dispersal of thiamine into a blood stream of the subject, wherein the thiamine migrates from a skin of the subject to the blood stream and from the blood stream to the skin of the subject providing protection from mosquitoes, flies, midges, or combinations thereof, and wherein the transdermal patch consists of:
      i. a backing;
      ii. 10 mg to 300 mg thiamine dispersed throughout a pressure-sensitive adhesive matrix, wherein a backing side of the pressure-sensitive adhesive matrix is disposed on at least a portion of the backing; and
      iii. a liner removable disposed on a skin side of the pressure-sensitive adhesive reservoir opposite the backing side; and
   b. removing the transdermal patch, wherein the thiamine continues to migrate from the blood stream to the skin of the subject providing protection from mosquitoes, flies, midges, or combinations thereof up to about six hours after removing the transdermal patch.

10. The method of claim 9, further comprising wearing the transdermal patch for 2 hours before protection is needed.

11. The method of claim 9, wherein the thiamine is systemically administered to the subject's blood stream through the subject's skin.

12. The method of claim 9, further comprising cleaning the skin of the subject prior to placing the transdermal patch on the skin of the subject.

13. The method of claim 9, wherein the transdermal patch has a skin contact area of about 5 cm$^2$.

14. The method of claim 9, wherein the adhesive comprises at least one of polyethylenes, polysiloxanes, polyisobutylenes, polyacrylates, polyacrylamides, polyurethanes, plasticized ethylene-vinyl acetate copolymers, and tack rubbers.

15. The method of claim 9, wherein the patch becomes transparent after thiamine is released transdermally into the skin.

* * * * *